United States Patent
Behnk

Patent Number: 5,284,624
Date of Patent: Feb. 8, 1994

[54] METHOD OF, AND APPARATUS FOR, TESTING AND MEASURING BLOOD CLOTTING TIME

[76] Inventor: Holger Behnk, Holitzberg 61, D-2000 Hamburg 62, Fed. Rep. of Germany

[21] Appl. No.: 938,210

[22] Filed: Aug. 31, 1992

Related U.S. Application Data

[62] Division of Ser. No. 428,358, Oct. 27, 1989.

[30] Foreign Application Priority Data

Oct. 31, 1988 [DE]  Fed. Rep. of Germany .... 3837078.6

[51] Int. Cl.⁵ .................. B01L 3/00; G01N 15/05
[52] U.S. Cl. ............................ 422/102; 422/72; 422/73; 422/104; 436/69
[58] Field of Search ............ 422/72, 73, 102, 104; 436/69

[56] References Cited

U.S. PATENT DOCUMENTS

| | | | |
|---|---|---|---|
| 3,233,975 | 2/1966 | McCormick . | |
| 3,504,376 | 3/1970 | Bednar et al. . | |
| 3,677,904 | 7/1972 | Fitzgerald | 435/293 X |
| 3,769,171 | 10/1973 | Grimes et al. | 435/293 X |
| 3,951,608 | 4/1976 | Trod | 422/102 X |
| 4,043,678 | 8/1977 | Farrell et al. | 436/165 |
| 4,081,242 | 3/1978 | Girolami | 436/69 |
| 4,357,301 | 11/1982 | Cassaday et al. | 422/102 |
| 4,371,498 | 2/1983 | Scordato et al. | 422/102 |
| 4,497,774 | 2/1985 | Scordato | 436/69 |
| 4,659,550 | 4/1987 | Schildknechk | 435/13 |
| 4,876,069 | 10/1989 | Jochimsem | 436/69 |
| 4,963,498 | 10/1990 | Hillman et al. | 436/69 |
| 5,051,370 | 9/1991 | Schulze et al. | 422/73 X |

FOREIGN PATENT DOCUMENTS 2383444 10/1978 France .
8702131 4/1987 PCT Int'l Appl. .

*Primary Examiner*—Jill A. Johnston
*Attorney, Agent, or Firm*—Chilton, Alix & Van Kirk

[57] ABSTRACT

The apparatus serves for testing and measuring blood clotting time. Blood or blood plasma (12) and a reagent (13) are introduced into a measuring cuvette (8). The clotting time is measured electro-optically with the aid of a stirring element (9) which is arranged in the measuring cuvette (8), can be attracted magnetically and is driven by a magnetic stirring device arranged outside the measuring cuvette (8). The method and apparatus are suitable for automatic measuring methods owing to the fact that blood plasma (12) and reagent (13) are introduced beside one another onto an essentially horizontal internal surface (10) of a measuring cuvette (8) provided with an opening above this surface (10), in that the measuring cuvette (8) and its contents are heated to the reaction temperature, in that the measuring cuvette is pivoted by essentially 90° in such a way that the internal surface (10) stands essentially perpendicular and plasma (12) and reagent (13) flow together, and in that the measurement is subsequently carried out.

13 Claims, 4 Drawing Sheets

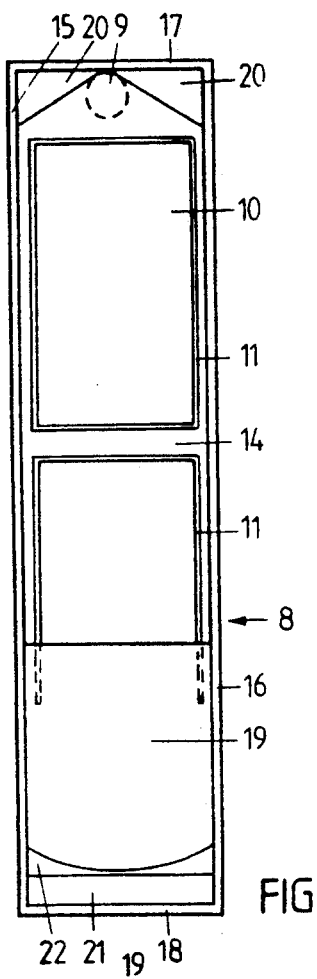
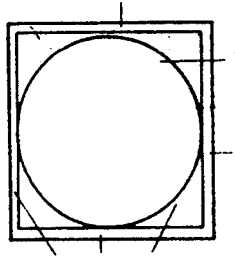
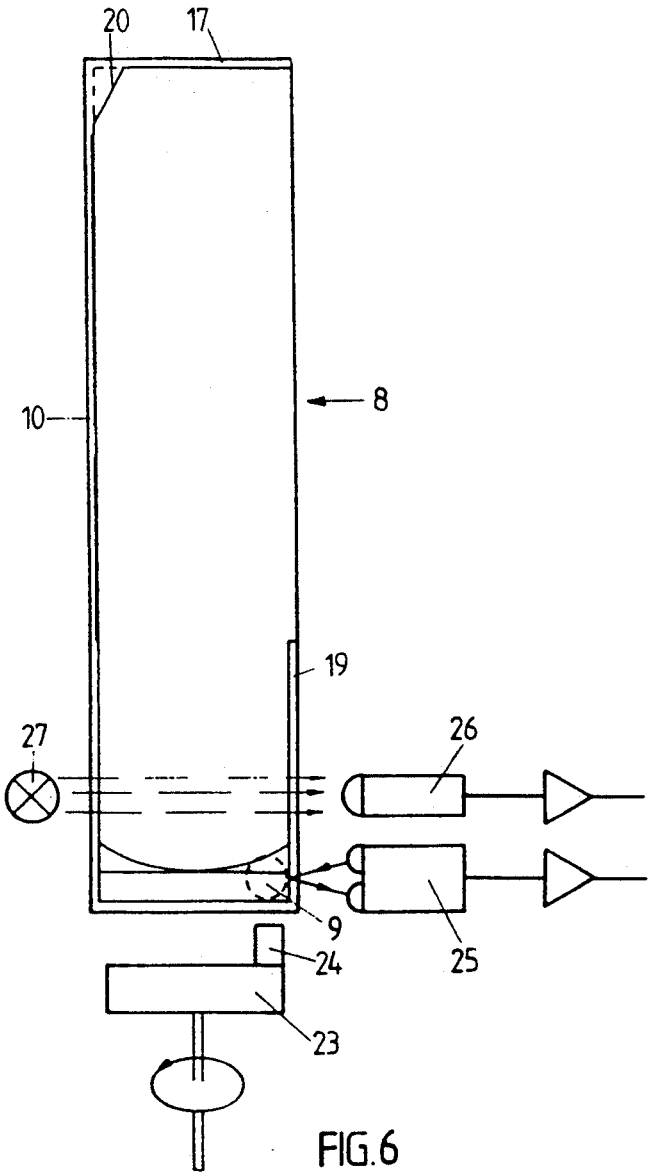

METHOD OF, AND APPARATUS FOR, TESTING AND MEASURING BLOOD CLOTTING TIME

This is a divisional of copending application Ser. No. 428,358 filed Oct. 27, 1989.

BACKGROUND AND SUMMARY OF THE INVENTION

The invention concerns a method and an apparatus for testing and measuring blood clotting time, in which blood or blood plasma and a reagent are introduced into a measuring cuvette and the clotting time is measured electro-optically with the aid of a stirring element which is arranged in the measuring cuvette, can be attracted magnetically and is driven by a magnetic stirring device arranged outside the measuring cuvette.

Methods and apparatuses of this type (DE-PS 3,127,560, EP-PS 0,090,192) permit very multifarious and dissimilar types of blood clotting time measurement. Although very accurate values are obtained, the costs of operation by trained personnel are necessarily high.

Although automatic methods for measuring blood clotting time are known, they cannot, however, be used for the measuring method with stirring elements mentioned at the beginning. Moreover, these methods have grave disadvantages. These disadvantages are connected with the fact that, on the one hand, the blood plasma and the reagents must be cooled before the measurement, whereas, on the other hand, the measurement must take place at a temperature which may have only very small deviations from 37° C. If the reagents are not kept at a temperature of 15° C., they partially decompose even after half an hour. On the other hand, if the temperature departs during measurement by only 1° from 37° C., there is already a measurement error of 10%.

In an automatic method for testing and measuring blood clotting time (brochure MLA Electra 800 from AHS/Deutschland GmbH), the measuring cuvettes, which have previously been filled with blood plasma by hand, are inserted into a carousel in which their temperature is controlled. When the cuvette is located at the appropriate station, the reagent is then filled into it by a pump from the cooled storage vessel through a plate-shaped element in which heating to 37° C. takes place. The plasma, which has been heated to 37° C., and the likewise heated reagent then meet here. The disadvantage consists, for one thing, in that the plasma still has to be filled into the measuring cuvettes by hand, and in that these measuring cuvettes then need to be inserted by hand into the carousel. A further disadvantage consists in that the plate-shaped heat exchangers take up a relatively high amount of reagent. When measurement is interrupted, it is then necessary for the reagent to be pumped back from these plate-shaped heat exchangers, since otherwise it decomposes. However, residual amounts subsequently dry on the walls, so that when restarting there is the danger of blockages or erroneous measurements. Consequently, the heat exchanger plates must be frequently replaced. Further, there is the danger of losses of relatively expensive reagent liquid. Moreover, a separate pump and a separate heat exchange surface are required for each reagent, so that with the named apparatus it is possible simultaneously to use only two reagents for one measurement. This number of reagents cannot be increased ad lib without excessive expenditure.

In a further method (brochure COAC-A-Mater-X2 from the firm Labordiagnostica Gödecke) the plate-shaped heat exchangers are dispensed with. Instead of these, the hoses for the reagents are lead through a plate-shaped element, which is at a temperature of 37° C. Here, after measurement has been interrupted the hoses can and/or must be cleaned or replaced, and this is likewise troublesome and expensive; there is also a high risk of erroneous measurements.

In a further previously known method (brochure ACL Automated Coagulation Laboratory from Instrumentation Laboratory), the plasma is automatically introduced into a cuvettes from a centrifuge tube. The reagents are also filled into the measuring cuvette automatically from cooled storage vessels. In this process, the transfer device can also be fed intermittently to a washing device. Subsequently, the space with the measuring cuvettes arranged on a centrifuge is closed off. The measuring cuvettes are then heated, and upon reaching a temperature of 37° C. are set into rapid rotation resulting in thorough mixing due to the centrifuge effect. This system likewise has various disadvantages.

For one thing, not all types of measurements are possible in the centrifuge. It is not possible to use any reagents which sediment, e.g. PTT reagent with kaolin. Again, the advantageous measurements with stirring elements are not possible. Moreover, the cuvettes must be absolutely leakproof, since otherwise at the high centrifuging rate of 1200 rpm liquid penetrates into the rotor space and contaminates it, and especially also contaminates the measuring devices. Finally, the measuring cuvettes cannot be removed automatically after the measurement, but must be taken out by hand.

The object of the invention consists in creating a method of the type mentioned at the beginning in which it is possible, by exploiting the advantages of the method with a stirring element, to conduct very many different tests with various reagents, changing rapidly from one reagent to another, the method being designed especially for automatic applications.

The object is achieved according to the invention in that blood plasma and reagent are introduced beside one another onto an essentially horizontal internal surface of a measuring cuvette provided with an opening above this surface, in that the measuring cuvette and its contents are heated to the reaction temperature, in that the measuring cuvette is pivoted in the measuring station by essentially 90° in such a way that the internal surface stands essentially perpendicular and plasma and reagent flow together, and in that the measurement is subsequently carried out.

DETAILED DESCRIPTION OF THE INVENTION

Thus, blood plasma and reagent are brought beside one another onto an essentially horizontal surface; in this connection, they are still initially at a temperature of, e.g., 15° C., at which no reactions yet take place. Subsequently, the measuring cuvette and its contents are then heated to the reaction temperature, although no reactions yet take place between plasma and reagent, since the two liquids are arranged beside one another and have not yet been mixed with one another. Subsequently, the measuring cuvette is then pivoted by essentially 90° in such a way that the internal surface stands essentially perpendicular, whereby plasma and reagent flow together. Subsequently, the measurement can then be carried out.

In this connection, the measuring cuvettes can be filled automatically with plasma and reagents, using only one pump. Problems of any sort concerning contamination, incubation or decomposition and the like do not arise, since the pumps and the feeder devices can be cooled. The measuring cuvette can then be conducted automatically into a heating station, where it is heated until it has reached a temperature of 37° C. The measurement can then subsequently be carried out, and in the process the advantages of the method with a stirring element can be exploited. Automatic removal then subsequently takes place. However, it is also possible, of course, to carry out the method by hand, if an appropriate apparatus for carrying out the method automatically is not available.

If the internal surface is initially inclined by a few degrees so that the end region of the internal surface, which is to be pivoted upwards during pivoting, lies deeper, than the remaining regions of the internal surface, the stirring element can initially be arranged in this deeper region. In this process, it is possible for the cuvette to be initially inclined, and then for the stirring element to be introduced into the deeper-lying region, or else for the stirring element to be introduced only so that it rolls to the desired position when the inclination is subsequently carried out. At the start of the pivoting process, the stirring element then falls into the reagent, and then into the plasma, and draws the latter downwards with it, the result being that a better mixing through is already achieved at the beginning. At the same time, the stirring element ensures a constant speed during transport of the reagent.

In other embodiments, the inclination will be chosen in precisely the opposite sense, so that when pivoting is carried out, the stirring element does not fall through the liquids, which could lead to splashes and undesired distribution of the liquids.

It has turned out to be especially advantageous if the stirring element is a metal ball.

If, after being pivoted, the measuring cuvette is dropped through a limited distance and strikes a stop face, the stirring element and the liquids are moved downwards impulsively, so that maximum amounts of the liquids are rapidly available here and can be mixed through.

It is possible without any difficulty to design the method like an assembly line in such a way that a plurality of measuring cuvettes are simultaneously conducted through the individual stations consecutively in sequence, and are subsequently removed.

A measuring cuvette for carrying out the method is characterized in that the internal surface for accepting plasma and reagent is essentially flat and is provided with surface structures preventing the liquids from flowing together. Because the internal surface is essentially flat, especially large amounts of plasma and reagent can be arranged beside one another but are prevented by the surface structures from flowing together already in this position of the measuring cuvette. If the measuring cuvette is subsequently pivoted, especially by approximately 95°, so that it subsequently stands perpendicular, these surface structures can no longer prevent a flowing together. This holds true especially if, after being pivoted, the cuvette is also dropped onto a stop face, a travel distance of 5 mm already being sufficient in this regard.

The surface structures can be small trough-like indentations for the liquids.

It is expedient for the surface structures to enclose regions separated from one another by an interface. In this connection, the liquids initially remain in the surface regions, and are separated from one another by the interface. The surface structures can be linear, ridge-like projections. However, the surface structures are especially simple to produce if they are linear notches.

If, in the immediately deeper-lying region, the internal surface is bounded at its rim by two boundary walls running together in the middle at an obtuse angle, a spherical stirring element will initially automatically roll into the middle of the edge, so that it then falls from this middle through the drops of liquid, and thereby carries along an especially large amount of liquids into the region in which the subsequent measurement is to be carried out. It is expedient to provide a central, cylindrical indentation on the surface on which the stirring element and the liquid meet, so that here the spherical stirring element can execute a circular movement, which is effected by the magnetic stirring device.

It is expedient to provide that the rim regions arranged outside the cylindrical recess are bevelled inwards, and in the position after the pivoting are bevelled downwards, these end regions having at least partially a smaller thickness than the diameter of the ball. These bevelled, especially spherical shell-shaped bevelled regions, ensure that the ball also rapidly reaches the predetermined cylindrical path even if it strikes the rim regions. If the end regions have a smaller thickness than the diameter of the ball, it is not only the liquid material in the cylindrical region which is stirred through by the ball; rather, a stirring effect is also exerted on the liquid portions located in the rim regions, especially in the corners of a rectangular measuring cuvette.

As already mentioned, the method and the apparatus have the advantage that it is possible to conduct very many different measurements simultaneously, to be precise a total of up to 13 determinations. It is easily possibly for the corresponding 13 reagents to be stored cooled, and for a complete clotting status to be made at any time. Whereas with the previously known automatic apparatuses there were three pumps, e.g. for the basic determinations of PT (prothrombin time) and PTT (partial thromboplastin time) which have sufficed for the clotting status for a long time, it is now also possible, in addition, to measure TT (thrombin time), and fibringoen which already happens in many hospitals. It is not possible to measure this for each patient in one pass using any previously known apparatus. If errors should arise in the case of this clotting status, it is, in addition, possible and necessary for the factors to be measured as well. This then adds up to the total of 13 determinations mentioned above.

If a plurality of measuring cuvettes are arranged in a common holder which has a toothed rack, this plurality of measuring cuvettes can be conducted through the various stations by a gear drive. In this way, a large number of tests can be carried out in a rapid sequence in a very rational way.

The invention is described on the basis of an exemplary embodiment with reference to the attached drawings, in which:

BRIEF DESCRIPTION OF THE DRAWINGS

FIG. 4 shows a top view of the measuring cuvette in a prone state;

FIG. 5 shows an end view of the same measuring cuvette;

FIG. 6 shows the measuring cuvette in the measuring station, the measuring cuvette being shown rotated about its longitudinal axis by 90° with respect to the representation of FIG. 4.

Figure 1:
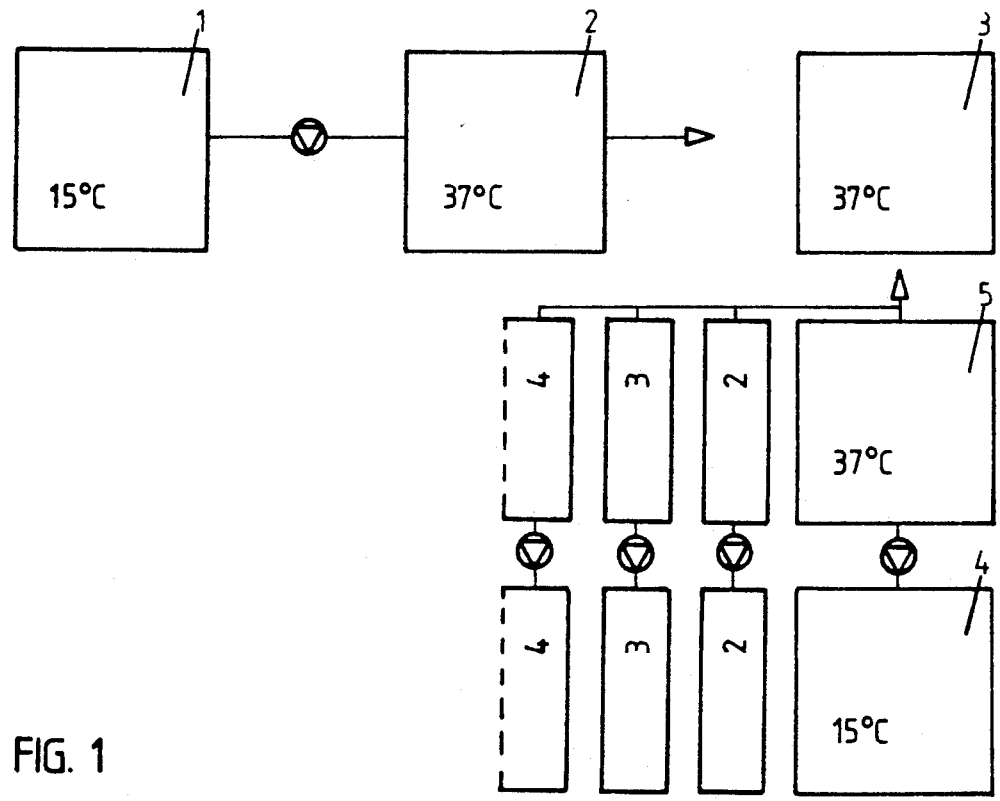
FIG. 1 shows the block diagram of a previously known automatic method.

In the block diagram of the previously known method of FIG. 1, the plasma is firstly kept at a temperature of 15° C. in step 1. Incubation to 37° C. then takes place in step 2 via surface contact with the incubator. Subsequently, the plasma or thus heated is then fed to the measuring station 3. On the other hand, the reagent is firstly kept in a station 4 at temperature of 15° C. Incubation to 37° C. then takes place in station 5 in plate-shaped heat exchangers or in the hoses. Subsequently, the reagent is then also brought into the measuring position 3.

Thus, in the case of automation one pump is required for plasma and reagent in step 1. In step 3 one pump is required for each reagent, and also a heat exchanger.

Figure 2:
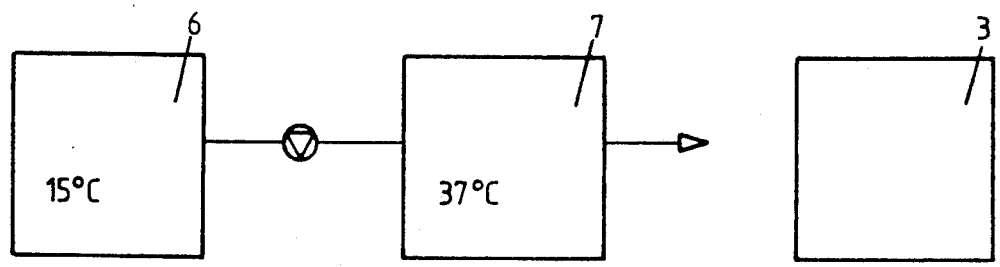
FIG. 2 shows the block diagram of the method according to the invention.

By contrast, the method according to the invention, which is represented in FIG. 2, is substantially simpler. Here, plasma and reagent are introduced beside one another into the measuring cuvette in step 6 at a temperature of 15° C. Subsequently, incubation to a temperature of 37° C. takes place in step 7. After the measuring cuvette has been pivoted, measurement then takes place in the measuring position 30. In the case of automation only one pump is required for plasma and reagent in step 6.

Figure 3:
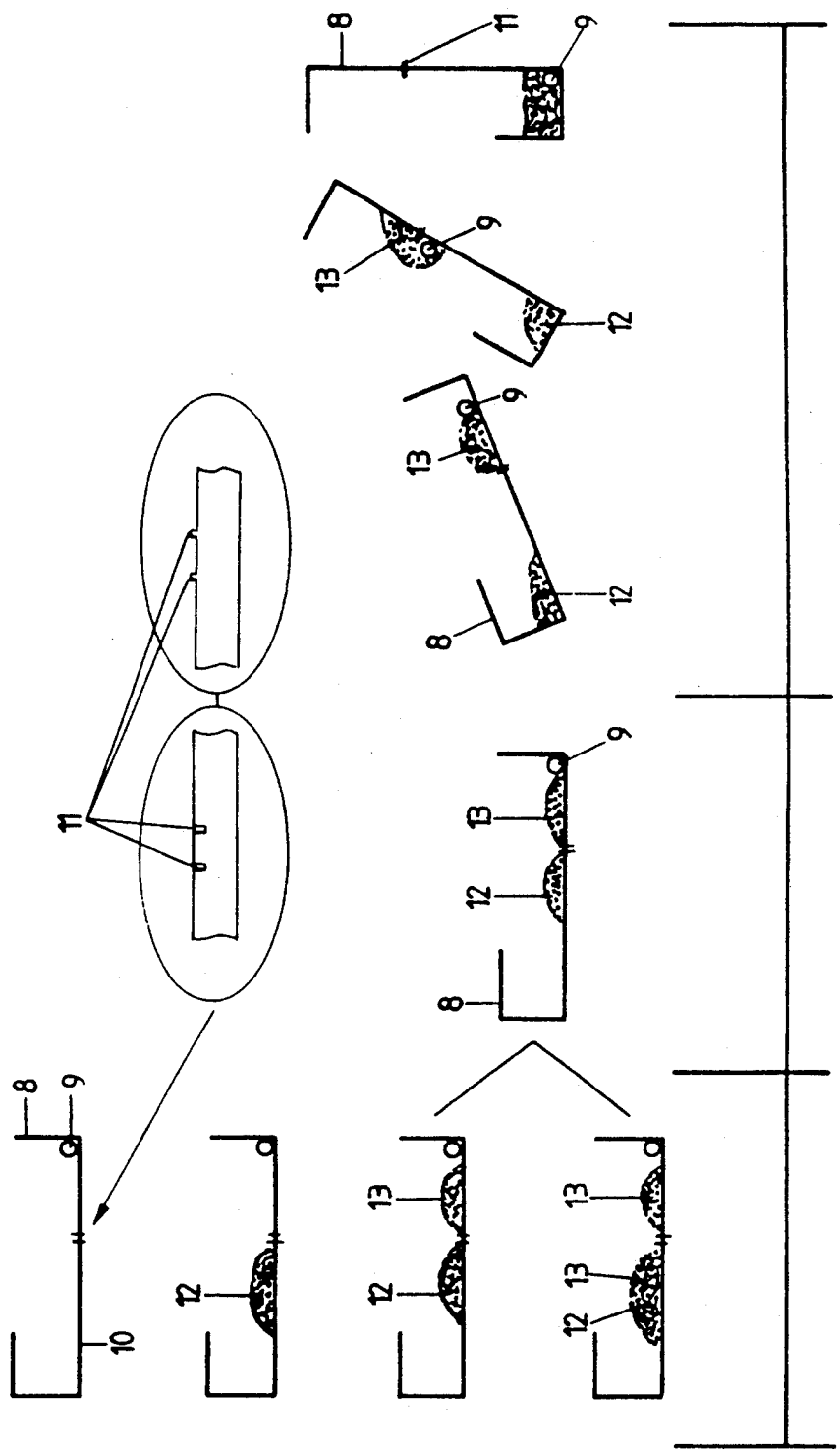
FIG. 3 shows the principle of the use of the measuring cuvette according to the invention.

The process according to the invention is shown more clearly in FIG. 3, which shows a side view in section of the measuring cuvette 8.

The measuring cuvette 8 is essentially in the shape of a parallelepiped, and has an opening on one of its faces, which occupies the main part of these faces. The cuvette is elongated and has an elongated cavity for receiving the blood or blood plasma and reagent. The measuring cuvette 8 thus has a shoe-like shape. In step 6, the stirring element 9 is first introduced in the form of a ball. In this process, the measuring cuvette is a little inclined, namely in such a way that the ball 9 is located at the lowest position. This inclination of the cuvette 8 is not absolutely necessary, and is also, not shown in FIG. 3. In the middle, the internal, elongated lower surface 10 of the cuvette 8 is subdivided by scribed indentations 11 or ridge-like projections, which extend linearly across the elongated lower surface in a transverse direction and will be described further in more detail in connection with FIG. 4. These indentations or projections 11 are also shown further magnified in FIG. 3. The plasma 12 is introduced to the left of these scribings 11. Subsequently, a reagent 13 is introduced to the right of the plasma 12 and the scribings 11 (from above to below in the representation of FIG. 3). If it is necessary, a further reagent can still subsequently be fed to the plasma 12.

The measuring cuvette 8 is brought in this condition into a further station, and incubated in step 7 to a temperature of 37° C. When the desired temperature has been reached, the cuvette 8 is then tilted in step 3, i.e. in the measuring station. As may be seen in the middle portion in the case of step 3, in this process the ball 9 penetrates into the reagent 13 and carries it along, so that in the right-hand position the ball 9 is located below, and plasma 12 and reagent 13 are thereby mixed. The clotting time is then measured here.

The cuvette 8 is shown more clearly in a top view in FIG. 4. The elongated lower surface 10 in the position of steps 6 and 7 of FIG. 3, onto which plasma 12 and reagent 13 are brought, is provided with mutually orthogonal notches, which border a closed area at least in the upper region in FIG. 4. The two regions, which are bordered at least partially by the notches 11, are separated by an intermediate region 14, so that the liquids whose flow is prevented by the notches 11, are clearly separated from one another, as long as the measuring cuvette 8 occupies its essentially horizontal position.

The side elongated generally parallel walls 15 and 16 are closed—as are the generally rectangular-shaped, generally parallel end faces 17 and 18, as shown in FIGS. 4-5. A portion of the upper face is closed off by an upper wall of cover 19 which is connected to end face 18 and side walls 15 and 16.

At the top in FIG. 4, the elongated lower surface 10 is bounded by sloping faces 20 which form an internal end wall with an indentation, so that the ball 9 is arranged in the middle of lower surface 10 if the cuvette 8 is inclined somewhat deeper in this region. The end face 18 lying opposite has a cylindrical recess 21, the rim regions 22 being bevelled at the corners, as may also be seen from FIG. 4. In this connection, FIG. 5 is a top view of the end face 18. The rim regions 22 have at lest partially a smaller thickness than the diameter of the ball. As shown in FIGS. 4 and 5, the surface area of elongated lower surface 10 is substantially larger than the surface area of the end faces 17 and 18.

Owing to the sloping faces 22, the ball falls into the cylindrical recess 21 when the measuring cuvette 8 is pivoted into the vertical position in FIG. 6. In this process, the ball 9 projects into the space above the cylindrical recess 21, so that it thoroughly mixes the liquid located in the lower region after the pivoting, when it is moved by a magnetic stirrer 23 with a permanent magnet 24.

The start of clotting can be determined by photoelectric devices, which are represented diagrammatically by 25 and 26. In this connection, the device 25 is a reflection measurement while the device 26 with a light source 27 is a transmission measuring device. These measuring devices are known from the patents named at the beginning, so that it is not necessary to describe them in more detail here. Obviously, the measuring cuvette is transparent, in order that the measurements can be carried out.

Figure 7:
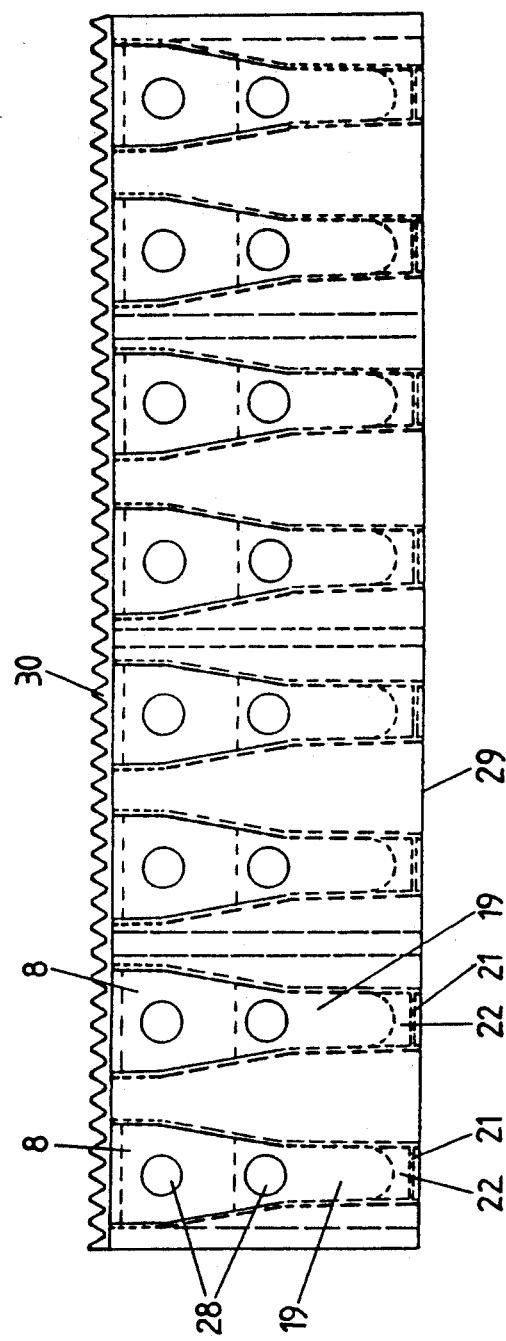
FIG. 7 shows a number of measuring cuvettes, which are grouped in a common holder with a toothed rack.

It is shown in FIG. 7 that a series of measuring cuvettes 8 are arranged beside one another in a holder 29, which carries a toothed rack 30 on its outside. The holder can be transported with the measuring cuvettes through the individual stations with the aid of this toothed rack 30 and of a gear drive (not shown), so that a large number of tests can be carried out in rapid sequence. In the embodiment shown in FIG. 7, the cover plate 19 also covers more or less the whole region of the measuring cuvette 8; the cover plate 19 has only two openings 28, through which plasma, reagent and ball can be put in.

I claim:

1. Measuring cuvette into which blood or blood plasma and a reagent are introduced for testing and measuring blood clotting time, comprising a bottom wall having a flat, substantially horizontal, elongated internal surface having a cross sectional area comprising a first portion and a second portion for accepting liquid plasma and liquid reagent, a pair of opposite, generally parallel elongated side walls, opposite first and second end walls including first and second internal end surfaces each having a substantially smaller cross sectional area than the elongated internal surface, an upper wall connected to the second end wall and the elongated side walls, the upper wall having an opening formed therein for receiving plasma on said first portion of said elongated internal surface and reagent on said second portion of said elongated internal surface, means formed on the elongated internal surface for preventing the plasma on the first portion and the reagent on the second portion from flowing together until the cuvette is pivoted, and a magnetically attracted stirring element disposed in the cuvette for promoting mixing of the plasma and reagent when the cuvette is pivoted.

2. Measuring cuvette according to claim 1, wherein said means for preventing the plasma on said first portion and reagent on said second portion from flowing together comprises at least one of indentations and trough-shaped regions formed on the elongated internal surface.

3. Measuring cuvette according to claim 1, wherein said means for preventing the plasma and reagent from flowing together includes linearly-extending projections or notches formed on the elongated internal surface which define an interface which separates the internal surface into at least said first portion and said second portion.

4. Measuring cuvette according to claim 1, wherein said means for preventing the plasma and reagent from flowing together comprises linearly-extending projections which project inward into the cuvette from the elongated internal surface.

5. Measuring cuvette according to claim 1, wherein said means for preventing the plasma and reagent from flowing together comprises linearly-extended notches formed on the elongated internal surface.

6. Measuring cuvette according to claim 1, wherein the first internal end surface comprises two sloping faces which are connected at an obtuse angle, forming an indentation in the middle of the first internal end surface.

7. Measuring cuvette according to claim 6, wherein the second internal end surface is generally perpendicular to the elongated internal surface and has a central, cylindrical or oval indentation.

8. Measuring cuvette according to claim 7, wherein the stirring element is a mixing ball with a diameter, and the second end face has rim regions arranged around the indentation which are bevelled inwards, the rim regions having at least partially a smaller thickness than the diameter of the ball.

9. Measuring cuvette according to claim 6, wherein the stirring element is a mixing ball and the mixing ball is positioned proximate the first internal end surface before the plasma and reagent flow together.

10. Measuring cuvette according to claim 6, wherein the stirring element is a mixing ball and the mixing ball is positioned proximate the second internal end surface before the plasma and reagent flow together.

11. Measuring cuvette according to claim 6, wherein the second internal end surface includes an indentation formed by a pair of sloping inner wall surfaces that are connected to each other at an obtuse angle.

12. An apparatus for measuring blood clotting time, the apparatus including a plurality of measuring cuvettes arranged in a holder, at least one of the cuvettes including a bottom wall having a flat, substantially horizontal, elongated internal surface for accepting liquid plasma and liquid reagent, the elongated internal surface having a cross sectional area comprising a first portion and a second portion, a pair of opposite, generally parallel elongated side walls, opposite first and second end walls including first and second internal end surfaces each having a substantially smaller cross sectional area than the elongated internal surface, an upper wall connected to the second end wall and the elongated side walls, the upper wall having an opening formed therein for receiving plasma onto said first portion of said elongated internal surface and reagent onto said second portion of said elongated internal surface, means formed on the elongated internal surface for preventing the plasma on the first portion and reagent on the second portion from flowing together until the cuvette is pivoted, and a magnetically attracted stirring element disposed in the cuvette for promoting mixing of the plasma and reagent when the cuvette is pivoted.

13. An apparatus according to claim 12, wherein the holder includes a toothed rack.

* * * * *